United States Patent
Mart et al.

(10) Patent No.: US 6,696,502 B1
(45) Date of Patent: *Feb. 24, 2004

(54) SLURRY HYDROCARBON SYNTHESIS WITH FRESH CATALYST ACTIVITY INCREASE DURING HYDROCARBON PRODUCTION

(75) Inventors: Charles John Mart, Baton Rouge, LA (US); Daniel Ray Neskora, Baton Rouge, LA (US)

(73) Assignee: ExxonMobil Research and Engineering Company, Annandale, NJ (US)

(*) Notice: Subject to any disclaimer, the term of this patent is extended or adjusted under 35 U.S.C. 154(b) by 404 days.

This patent is subject to a terminal disclaimer.

(21) Appl. No.: 09/587,148

(22) Filed: Jun. 2, 2000

(51) Int. Cl.[7] .......................... C07C 27/00; B01J 20/34
(52) U.S. Cl. .................. 518/709; 518/700; 518/715; 502/20
(58) Field of Search ................. 518/700, 715, 518/709; 502/20

(56) References Cited

U.S. PATENT DOCUMENTS

| | | | |
|---|---|---|---|
| 5,283,216 A | 2/1994 | Mitchell | 502/30 |
| 5,292,705 A | 3/1994 | Mitchell | 502/325 |
| 5,811,363 A | 9/1998 | Leviness et al. | 502/21 |
| 5,811,468 A | 9/1998 | Chang et al. | 518/700 |
| 5,817,702 A | 10/1998 | Behrmann et al. | 518/700 |
| 5,821,270 A | 10/1998 | Chang et al. | 518/700 |
| 5,844,005 A | 12/1998 | Bauman et al. | 518/700 |
| 5,958,986 A | 9/1999 | Mart et al. | 518/709 |
| 6,323,248 B1 * | 11/2001 | Mart et al. | 518/709 |

FOREIGN PATENT DOCUMENTS

WO   WO9717137   5/1997   ............ B01J/37/18

* cited by examiner

Primary Examiner—J. Parsa
(74) Attorney, Agent, or Firm—Mark D. Marin (57) ABSTRACT

Fresh catalyst particles are added to a slurry hydrocarbon synthesis reactor and their activity increased by contact with hydrogen in-situ in the slurry in a catalyst activity increasing means, while the reactor is producing hydrocarbons. The means may be a simple, vertically oriented and hollow tube, open at the top and bottom, into which slurry and a hydrogen treat gas are passed. The treat gas acts as a lift gas which provides slurry circulation into and out of the means and back into the slurry body, while increasing the activity of the catalyst particles. During the activity increase of the fresh catalyst, partially and reversibly activated catalyst particles are rejuvenated. The activity increasing means may be inside the reactor and at least partially immersed in the slurry or external of the reactor, or both.

19 Claims, 2 Drawing Sheets

SLURRY HYDROCARBON SYNTHESIS WITH FRESH CATALYST ACTIVITY INCREASE DURING HYDROCARBON PRODUCTION

BACKGROUND OF THE DISCLOSURE

1. Field of the Invention

The invention relates to a slurry hydrocarbon synthesis process, which includes increasing the activity of fresh catalyst in-situ in the slurry liquid, during the synthesis reaction. More particularly the invention relates to a slurry Fischer-Tropsch hydrocarbon synthesis process for producing hydrocarbons from a synthesis gas, wherein the activity of fresh synthesis catalyst added to the slurry reactor is increased in-situ in the slurry during the synthesis reaction.

2. Background of the Invention

The slurry Fischer-Tropsch hydrocarbon synthesis process is now well known and documented, both in patents and in the technical literature. This process comprises passing a synthesis gas which comprises a mixture of $H_2$ and CO, up into a reactive slurry comprising a hot, synthesized hydrocarbon liquid, in which a suitable, particulate Fischer-Tropsch type of catalyst is dispersed and suspended, at reaction conditions effective for the $H_2$ and CO to react and form liquid hydrocarbons. The hydrocarbon liquid is continuously withdrawn from the reactor and upgraded by one or more upgrading steps, which include fractionation and conversion operations such as hydroconversion, in which a portion of the molecular structure of at least some of the hydrocarbon molecules is changed. The upgraded products may include, for example, a syncrude, various fuels and lubricating oil fractions and wax. During the synthesis reaction, the presence of reversibly deactivating catalyst species present in the synthesis gas, such as $NH_3$ and HCN, causes a reduction in catalyst activity. This activity loss is reversible and may be restored in-situ in the reactor by rejuvenation, as is known and disclosed, for example, in U.S. Pat. Nos. 5,283,216; 5,811,363; 5,811,468; 5,817,702; 5,821,270; 5,844,005 and 5,958,986. Catalyst rejuvenation is achieved by passing hydrogen or a hydrogen treat gas into the bottom of a vertically oriented, hollow conduit or tube immersed in the slurry or external of the synthesis reactor in a separate vessel. This sets up a slurry circulation in the tube, in which the hydrogen gas contacts the catalyst particles in the slurry liquid, thereby rejuvenating them by restoring at least part of their activity. Some of the activity loss is permanent, which ultimately requires catalyst regeneration or replacement. One of the advantages of the slurry process, is the ability to add and remove catalyst without taking the reactor offline and thereby stopping the synthesis reaction. U.S. Pat. No. 5,292,705 discloses that the activity of a fresh Fischer-Tropsch type of hydrocarbon synthesis catalyst can be increased by treatment with hydrogen in a hydrocarbon liquid, including in-situ in the hydrocarbon synthesis slurry in the synthesis reactor. The hydrogen treatment for increasing the catalytic activity is preferably conducted in the absence of CO. Thus, in this process, if the catalyst activity is increased by treatment in-situ in the hydrocarbon synthesis slurry in the slurry synthesis reactor, the synthesis reactor is not producing hydrocarbons while the activity of the fresh catalyst is increased. It would be an improvement to the art if the activity of fresh catalyst added to the reactor could be increased while the reactor is producing hydrocarbons and without adversely effecting the selectivity or productivity of the synthesis reaction.

SUMMARY OF THE INVENTION

The present invention relates to a process for increasing the activity, and therefore the productivity, of a fresh hydrocarbon synthesis catalyst above its initial value, by contacting it with hydrogen or a hydrogen treat gas, insitu in the hydrocarbon synthesis slurry used for synthesizing hydrocarbons in the slurry Fischer-Tropsch hydrocarbon synthesis reactor, while the reactor is producing hydrocarbons from the synthesis gas feed. This is achieved by adding the fresh catalyst to the hydrocarbon synthesis slurry in, or external of, the synthesis reactor and circulating a portion of the slurry containing the fresh catalyst up through one or more catalyst activity increasing means, the interior of which is isolated from the slurry body in the synthesis reactor. Hydrogen or a hydrogen treat gas is passed into the means, in which it contacts the fresh catalyst particles in the flowing slurry and increases their activity. By fresh catalyst is meant one that is new and has not been used, or has been in use only for a relatively short period of time and has an activity of at least 85%, preferably at least 90% and more preferably at least 95% of the initial value of a new and unused catalyst. By initial value is meant the lined out activity level the fresh catalyst exhibits when first added to the slurry, extrapolated back to zero time. The activity is calculated based on the extent of CO conversion and, for a given catalyst, is effected by the space velocity, temperature, and partial pressure of the reactants and reaction products, as well as the hydrodynamics in the slurry reactor. Irrespective of whether the slurry reactor is operated as a dispersed or slumped bed, the mixing conditions in the slurry will typically be somewhere between the two theoretical conditions of plug flow and back mixed. In contrast to the process disclosed in U.S. Pat. No. 5,292,705, in which the synthesis reactor is off-line and not producing hydrocarbons while increasing the activity of the fresh catalyst in-situ in the slurry in the synthesis reactor, in the process of the invention the activity of the fresh catalyst is increased in-situ in the slurry in the synthesis reactor without interrupting or interfering with the hydrocarbon synthesis reaction. This is made possible, because the catalyst activity increasing zone, even if it is wholly immersed in the slurry body in the synthesis reactor, is isolated from it. The catalyst activity increasing process of the invention eliminates the need for (i) the addition of heat to the reactor, (ii) additional hydrogen capacity and (iii) compressors to deliver sufficient hydrogen to the reactor to maintain slurry circulation and catalyst dispersion in the slurry liquid while increasing the catalyst activity.

In the process of the invention, the fresh catalyst in the form of solid particles or slurried in an appropriate hydrocarbon liquid, is added to the hydrocarbon synthesis slurry. The hydrocarbon synthesis slurry containing the fresh catalyst is contacted with a hydrogen treat gas in one or more catalyst activity increasing zones, in which it contacts the fresh catalyst particles and increases their activity. The slurry containing the activity increased catalyst is then returned to the hydrocarbon synthesis slurry body (hereinafter "slurry body") in the hydrocarbon synthesis reactor. In one embodiment, the fresh catalyst is added to the hydrocarbon synthesis slurry, by adding it to the slurry body in the reactor, with a portion of the slurry body, now containing the fresh catalyst, circulated from the slurry body up through and out of the one or more catalyst activity increasing zones and back into the slurry body. In another embodiment, the fresh catalyst is added to the hydrocarbon synthesis slurry in the one or more zones, as the hydrocarbon synthesis slurry and hydrogen treat gas pass up and through the zones, with the slurry containing the activity increased fresh catalyst then returned back to the slurry body in the synthesis reactor. Thus, the expression "the fresh catalyst is added to the hydrocarbon synthesis slurry" is meant to include one or both of these two embodiments. By "hydrocarbon synthesis slurry" is meant either the slurry body in the synthesis reactor, or slurry withdrawn from the slurry body with or without gas bubble removal prior to passing it into the one or more catalyst activity increasing zones or means. The hydrocarbon synthesis slurry comprising the slurry body in the synthesis reactor comprises catalyst particles and gas bubbles dispersed in a hydrocarbon slurry liquid.

The catalyst activity increasing means may comprise a hollow, elongated and substantially vertically oriented fluid conduit, such as a hollow tube, open at both ends for fluid to flow through, the interior of which comprises the activity increasing reaction zone. The one or more activity increasing reaction zones may be inside the synthesis reactor, external of the reactor and in fluid communication with the slurry body in the reactor, or both. Irrespective of which of these three modes is employed in the process of the invention, the hydrocarbon synthesis slurry and catalyst activity increasing hydrogen in the activity increasing reaction zone are isolated from the slurry body in the reactor. Slurry circulation up through the means is achieved by the lifting action of the hydrogen treat gas and, therefore, the activity increasing means may be viewed as a form of lift tube reactor. Circulation of the hydrocarbon synthesis slurry containing the fresh catalyst up through and out of the zone, and back into the slurry body in the synthesis reactor continues as long as the hydrogen flow up through the activity increasing zone is maintained. After the activity of the fresh catalyst is achieved, the hydrogen flow up through the catalyst activity increasing zone may be continued for catalyst rejuvenation. Thus, the same means and zone may be used for increasing the activity of the fresh catalyst and for catalyst rejuvenation. As a practical matter, the fresh catalyst activity increase occurs simultaneously with rejuvenation and it is preferred to remove at least a portion of the gas bubbles, which contain unreacted CO, from the slurry before it is passed into the activity increasing zone. To this extent, any means which permits rejuvenation while the synthesis reactor is producing hydrocarbons, such as those referred to above, can also be used for increasing the activity of the fresh catalyst and preferably those which remove gas bubbles from the slurry, before it is passed into the reaction zone in the means.

In one embodiment, the invention relates to a process for increasing the activity of a fresh hydrocarbon synthesis catalyst in a hydrocarbon synthesis slurry, which comprises (i) contacting the slurry with a hydrogen treat gas in one or more catalyst activity increasing reaction zones, to increase the activity of the fresh catalyst in the slurry, and (ii) passing the slurry containing the activity increased catalyst into a slurry body in a hydrocarbon synthesis reactor while the reactor is producing hydrocarbons from synthesis gas, wherein the slurry body comprises a hydrocarbon synthesis slurry comprising hydrocarbon synthesis catalyst particles and bubbles of synthesis gas in a hydrocarbon slurry liquid. Another embodiment relates to a slurry Fischer-Tropsch hydrocarbon synthesis process for producing hydrocarbons from a synthesis gas comprising a mixture of $H_2$ and CO, wherein fresh synthesis catalyst is added to the hydrocarbon synthesis slurry and its activity is increased in-situ, in the hydrocarbon synthesis slurry, while the hydrocarbon synthesis reactor is producing hydrocarbons, by withdrawing a portion of hydrocarbon synthesis slurry from the slurry body and passing it and hydrogen or a hydrogen treat gas into one or more catalyst activity increasing reaction zones at least partially immersed in the slurry body in the synthesis reactor, in which the hydrogen contacts and increases the activity of the fresh catalyst. The slurry containing the activity increased catalyst passes out of the zone and back into the slurry body with which it mixes. It is preferred to remove at least a portion of the gas bubbles from the slurry before it enters the one or more activity increasing zones. It is more preferred to also remove at least a portion of any particulate solids present in the slurry, in addition to gas bubble removal, before it enters the one or more zones. In addition to unreacted synthesis gas, the gas bubbles also contain water vapor, hydrocarbon reaction products that are gaseous at the synthesis conditions, and inerts such as nitrogen and $CO_2$. In a further embodiment, a portion of the hydrocarbon synthesis slurry containing fresh catalyst is circulated into and through one or more catalyst activity increasing zones external of the synthesis reactor, in which hydrogen contacts and increases the activity of the fresh catalyst particles in the slurry, with the slurry then returned back to the slurry body in the reactor. In a more specific embodiment, the invention is a slurry hydrocarbon synthesis process, which comprises:

(a) passing a synthesis gas comprising a mixture of $H_2$ and CO up into a slurry body comprising a hydrocarbon synthesis slurry, in a hydrocarbon synthesis reactor, wherein the slurry comprises a particulate Fischer-Tropsch catalyst and bubbles of the synthesis gas dispersed in a hydrocarbon liquid, at reaction conditions effective for the $H_2$ and CO in the synthesis gas to react and form hydrocarbons, at least a portion of which are liquid at the reaction conditions and which comprise the slurry hydrocarbon liquid;

(b) adding fresh catalyst particles to the hydrocarbon synthesis slurry, and (c) passing a hydrogen treat gas and the hydrocarbon synthesis slurry containing the fresh catalyst particles through one or more catalyst activity increasing zones, in which the hydrogen in the treat gas contacts the fresh catalyst particles in the slurry, which increases the activity of at least a portion of them, wherein the slurry containing the activity increased catalyst exits the one or more zones and is passed into the slurry body in the reactor, and wherein the activity increase occurs while the synthesis reactor is producing hydrocarbons from the synthesis gas.

The passing and contacting will typically and preferably continue for a time sufficient to increase the activity of substantially all of the fresh catalyst particles added to the hydrocarbon synthesis slurry. Preferably at least a portion of the gas bubbles are removed from the slurry before it passes into the zone. Sufficient hydrogen or hydrogen treat gas is introduced into the zone to act as a lift gas and preferably provide slurry circulation into and through the activity increasing zone without the need for a mechanical slurry pump. The hydrocarbon slurry liquid produced in the reactor is separated from the catalyst particles either continuously or intermittently, and upgraded by one or more upgrading steps. These include one or more of fractionation and/or conversion operations, such as hydroconversion, in which the molecular structure of at least some the hydrocarbon molecules is changed. To the extent that the fresh catalyst is added to a hydrocarbon synthesis slurry containing reversibly deactivated catalyst particles, the activity increase of the fresh catalyst in the zone occurs simultaneously with catalyst rejuvenation. It has been found that both increasing the activity of fresh catalyst and catalyst rejuvenation will occur with CO present in the zone. However, the less the amount of CO present, the faster and more efficient will be the activity increase. Thus, if CO is present, the CO content of the total amount of the activity increasing hydrogen or hydrogen treat gas passed into the zone is preferably less than 10 mole % and the $H_2$ to CO mole ratio in the gas is preferably greater than 3:1, more preferably greater than 4:1 and most preferably greater than 5:1. The offgas produced by the activity increasing or activity increasing and rejuvenation reactions in the zone will contain unreacted hydrogen. Those skilled in the art will appreciate that rejuvenation results in an activity increase of reversibly deactivated catalyst particles in the slurry. However, while there may be some overlap, in the context of the invention the term "activity increase" is used to refer to fresh catalyst particles added to the slurry, while "rejuvenation" refers to increasing the activity of reversibly deactivated catalyst particles.

DETAILED DESCRIPTION

The term "fresh catalyst" has been defined above as including a new, previously unused active catalyst, as well as a catalyst that has seen some use, but retains at least 85%, preferably at least 90% and more preferably at least 95% of the initial activity exhibited by the catalyst when new and previously unused. New catalyst means a newly manufactured or regenerated catalyst, with the difference being that a regenerated catalyst is derived from an irreversibly deactivated catalyst that has been treated to restore catalytic activity. Regeneration refers to treatments used to restore catalytic activity to an irreversibly deactivated catalyst, which cannot be rejuvenated simply by contact with hydrogen. Unlike rejuvenation, regeneration treatments involve a number of steps which include, for example, burning off carbon, selective leaching, redispersion of agglomerated components, calcination or oxidation, reduction and the like, all of which is well known and documented in the literature. Fischer-Tropsch catalysts useful in a slurry Fischer-Tropsch hydrocarbon synthesis process are well known and are prepared by compositing the catalytic metal component(s) with one or more catalytic metal support components, which may or may not include one or more suitable zeolite components, by ion exchange, impregnation, incipient wetness, compositing or from a molten salt, to form the catalyst precursor. Such catalysts typically include a composite of at least one Group VIII catalytic metal component supported on, or composited with, with at least one inorganic refractory metal oxide support material, such as silica, titania, alumina, amorphous silica-alumina, zeolites and the like. The elemental Groups referred to herein are those found in the Sargent-Welch Periodic Table of the Elements, © 1968 by the Sargent-Welch Scientific Company. The precursor must be activated to form the catalyst. Typical activation methods include oxidation followed by reduction in flowing hydrogen, multiple oxidation-reduction cycles (i.e., R-O-R) and reduction without prior oxidation. Suitable Fischer-Tropsch reaction types of catalyst comprise, for example, one or more Group VIII catalytic metals such as Fe, Ni, Co, and Ru. "In one embodiment the catalyst comprises catalytically effective amounts of Co and one or more of Re, Ru, Fe, Ni, Th, Zr, Hf, U, Mg and La on a suitable inorganic support material, preferably one which comprises one or more refractory metal oxides. Preferred supports for Co containing catalysts comprise titania, particularly when employing a slurry hydrocarbon synthesis process in which higher molecular weight, primarily paraffinic liquid hydrocarbon products are desired. Useful catalysts and their preparation are known and illustrative, but nonlimiting examples may be found, for example, in U.S. Pat. Nos. 4,492,774; 4,568,663; 4,663,305; 4,542,122; 4,621,072 and 5,545,674.

The hydrogen gas used for increasing the activity of the fresh catalyst can be high purity hydrogen or it can be hydrogen mixed with inert gases such as nitrogen, methane, $CO_2$ and the like. Thus, in the context of the invention, the terms "hydrogen" and "hydrogen treat gas" are synonymous and may be either pure hydrogen or a hydrogen-containing treat gas which is a treat gas stream containing hydrogen, along with other gas or gasses (e.g., nitrogen and light hydrocarbons such as methane, $CO_2$ and $C_4$. gasses) which will not adversely affect either the reactions or the products. The hydrogen partial pressure in the treat gas must be sufficient to increase the activity of the fresh catalyst particles and also rejuvenate reversibly deactivated catalyst particles in the slurry. Preferably it will be free of CO and water vapor. Tail gas from the catalyst activity increasing reaction, which comprises a mixture of hydrogen, methane, nitrogen and carbon dioxide, may also form part of the treat gas, provided that catalyst deactivating species are removed first.

In a slurry hydrocarbon synthesis process conducted under nonshifting conditions, which is the process used in the practice of the invention, the mole ratio of the $H_2$ to CO in the synthesis gas may broadly range from about 0.5 to 4, but the stoichiometric consumption mole ratio is typically about 2.1/1. The synthesis gas comprising a mixture of $H_2$ and CO is injected or bubbled up into the bottom of the slurry body in the reactor, in which the $H_2$ and CO react in the presence of the particulate Fischer-Tropsch hydrocarbon synthesis catalyst in the slurry liquid, at conditions effective to form hydrocarbons, a portion of which are liquid at the reaction conditions and which comprise the hydrocarbon slurry liquid. The synthesized hydrocarbon liquid is separated from the catalyst particles as filtrate by means such as simple filtration, although other separation means can be used. Some of the synthesized hydrocarbons are vapor and pass out of the hydrocarbon synthesis reactor as overheads or tail gas, along with unreacted synthesis gas and gaseous reaction products. Some of these overhead hydrocarbon vapors are typically condensed to liquid and combined with the hydrocarbon liquid filtrate. Thus, the initial boiling point of the filtrate will vary depending on whether or not some of the condensed hydrocarbon vapors have been combined with it. Slurry hydrocarbon synthesis process conditions vary somewhat depending on the catalyst and desired products. Typical conditions effective to form hydrocarbons comprising mostly $C_{5+}$ paraffins, (e.g., $C_{5+}$-$C_{200}$) and preferably $C_{10+}$ paraffins, in a slurry hydrocarbon synthesis process employing a catalyst comprising a supported cobalt component include, for example, temperatures, pressures and hourly gas space velocities in the range of from about 320–600° F., 80–600 psi and 100–40,000 V/hr/V, expressed as standard volumes of the gaseous CO and $H_2$ mixture (60° F., 1 atm) per hour per volume of catalyst, respectively. Such $C_{5+}$ and $C_{10+}$ hydrocarbons are sometimes referred to as Fischer-Tropsch wax, because these fractions are waxy solids at room temperature. It is preferred to conduct the synthesis reaction under conditions which maximize production of $C_{5+}$ hydrocarbons and more preferably $C_{10+}$ hydrocarbons, particularly when hydrocarbons boiling in the distillate fuels and lubricants ranges are desired.

Synthesis gas made from hydrocarbon feedstocks which contain nitrogen (i.e., natural gas) or nitrogen containing compounds (i.e., resids, coal, shale, coke, tar sands, etc.) invariably contains HCN and/or $NH_3$ which rapidly, but reversibly, deactivate the catalyst. Catalyst deactivation by these species is reversible and catalytic activity is restored (the catalyst rejuvenated) by contacting the deactivated catalyst with hydrogen, as is known. The activity of reversibly deactivated catalyst particles in the hydrocarbon synthesis slurry may be intermittently or continuously rejuvenated by contacting the slurry with hydrogen or a hydrogen containing treat gas to form a rejuvenated catalyst slurry as is known and disclosed for example, in the patents referred to under the Background, and briefly discussed above. Known slurry catalyst rejuvenation means will, in addition to rejuvenating partially reversibly deactivated catalyst particles, also increase the activity of fresh catalyst added to the slurry passing up through the rejuvenation zone with the partially deactivated particles. Thus, the present invention also comprises a process for simultaneously (i) increasing the activity of fresh catalyst particles and (ii) rejuvenating reversibly deactivated catalyst particles in the hydrocarbon synthesis slurry, by passing a hydrogen treat gas and the slurry containing both types of catalyst particles up through the rejuvenating or activity increasing reaction zone, at conditions of temperature and pressure similar to those in the hydrocarbon synthesis reactor, and back into the slurry body in the synthesis reactor.

Figure 1:
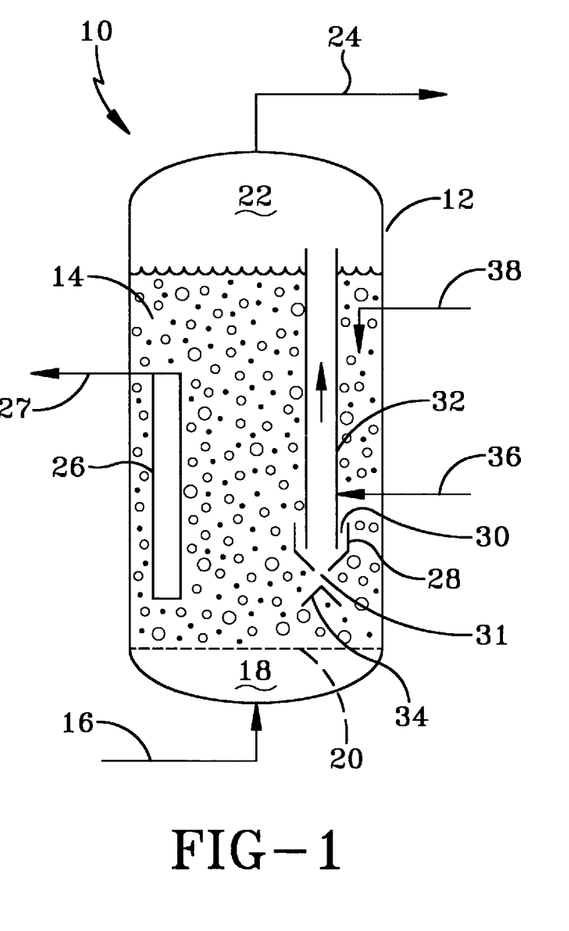
FIG. 1 is a simple schematic view of a slurry type Fischer-Tropsch reactor containing a vertical hollow fluid conduit or tube within, for increasing the activity of fresh catalyst added to the slurry according to the practice of the invention.

FIG. 1 is a simplified schematic briefly illustrating a slurry type hydrocarbon synthesis reactor 10, which comprises a cylindrical vessel 12 containing a three-phase reactive hydrocarbon synthesis slurry (the slurry body) 14 within. Feed line 16 passes the synthesis gas feed up into the plenum space 18 at the bottom of the reactor, from where it passes up into the hydrocarbon synthesis slurry by means of a gas distributor grid, briefly illustrated by the dashed line 20. Except for the gas injecting jets (not shown) extending through and horizontally arrayed across its surface, grid 20 is impervious to solids, liquid and gas. The gas bubbles in the slurry are indicated by the hollow circles, while the dispersed catalyst particles are indicated by the solid dots. As the bubbles of synthesis gas rise up through the slurry, the $H_2$ and CO in the gas reacts in the presence of the catalyst particles to produce hydrocarbons, a portion of which are liquid at the reaction conditions and which comprise the slurry hydrocarbon liquid. The gaseous products of the synthesis reaction and unreacted synthesis gas rise up into the top space 22 of the reactor, over the slurry and are withdrawn as overheads via line 24. A filter means immersed in the slurry and briefly illustrated as box 26, enables continuous or intermittent withdrawal of the synthesized hydrocarbon liquid from the reactor, via line 27. A simple vertical, hollow tube or conduit 32 open at both ends, provides the means for increasing the activity of the fresh added catalyst. The interior of the tube comprises the dual catalyst activity increasing and rejuvenating reaction zone, and means 32 functions as a form of lift tube reactor. An upwardly opening, generally bucket or cup-shaped means 28, for removing gas bubbles from slurry passing into the bottom of 32, is positioned partially over the bottom portion of 32, as shown. The cylindrical sidewall of 28 peripherally surrounds the bottom portion of 32, to provide an annular space 30, between the exterior of 32 and the interior of 28. The uprising synthesis gas bubbles are not able to contact the slurry in space 30. As a consequence, gas bubbles in the slurry passing through 30 are able to pass up into the slurry body above, thereby reducing the gas bubble content of slurry passing up into 32. The bottom of 28 is sloped at an angle greater than the angle of repose of the solid particles in the slurry, so that any disengaged slurry particles flow down and out via centrally located orifice 31. Thus, the combination of the sloped bottom and orifice 31 prevents the build-up of particulate solids in 28. A simple baffle 34 prevents uprising synthesis gas bubbles from entering up into the tube and means 28, as this would otherwise interfere with the effectiveness of (i) the gas bubble removal, (ii) increasing the activity of the fresh catalyst particles and (iii) catalyst rejuvenation. This combination of a vertical tube having a gas removal means like 28 is known and disclosed in U.S. Pat. No. 5,817,702 the disclosure of which is incorporated herein by reference. The hydrogen treat gas is injected up into the tube via a gas line 36, located proximate the bottom. The treat gas also acts as a lift gas to circulate the hydrocarbon synthesis slurry up through and out of the tube, without the need for a mechanical pump. In this embodiment, the top of the tube is shown as being slightly above the top of the slurry body, so that gas disengages from the slurry containing the activity increased fresh catalyst particles, with the gas-reduced slurry then passing back down into the slurry body 14. This is preferred, so that any catalyst deactivating species formed as gaseous reaction products of the rejuvenation pass up and out of the reactor, without being introduced into the slurry body as possible contaminants. A fresh catalyst feed line 38, injects a slurry comprising fresh catalyst particles into the slurry body 14 in the reactor, as needed. The hydrogen treat gas flow up the lift tube 32 circulates the hydrocarbon synthesis slurry in the reactor, which contains fresh catalyst particles and rejuvenable, partially deactivated catalyst particles from the slurry body, through the gas bubble removal means 28 and up into the interior of the tube, in which the hydrogen contacts the catalyst particles in the upflowing slurry to increase the activity of the fresh particles and rejuvenate reversibly deactivated particles. The slurry then passes out of the top of the tube and back into the slurry body, with which it mixes. The hydrogen flow into the tube continues at least until the desired level of activity increase is achieved and will typically be continued to maintain catalyst rejuvenation. More typically, the lift tube or means will be operating for catalyst rejuvenation before fresh catalyst is added and will continue to operate for rejuvenation after the activity of the fresh catalyst has been increased. This is typically when the overall activity reaches a maximum. While not shown, one or more vertical, gas bubble disengaging downcomers, of the type disclosed and claimed in U.S. Pat. No. 5,382,748 the disclosure of which is incorporated herein by reference, may be positioned inside the slurry body, to improve the vertical catalyst distribution. In a still further embodiment, mixing means, not shown, may be located in the activity increasing means, to improve mixing of the hydrogen gas and slurry flowing within.

Figure 2:
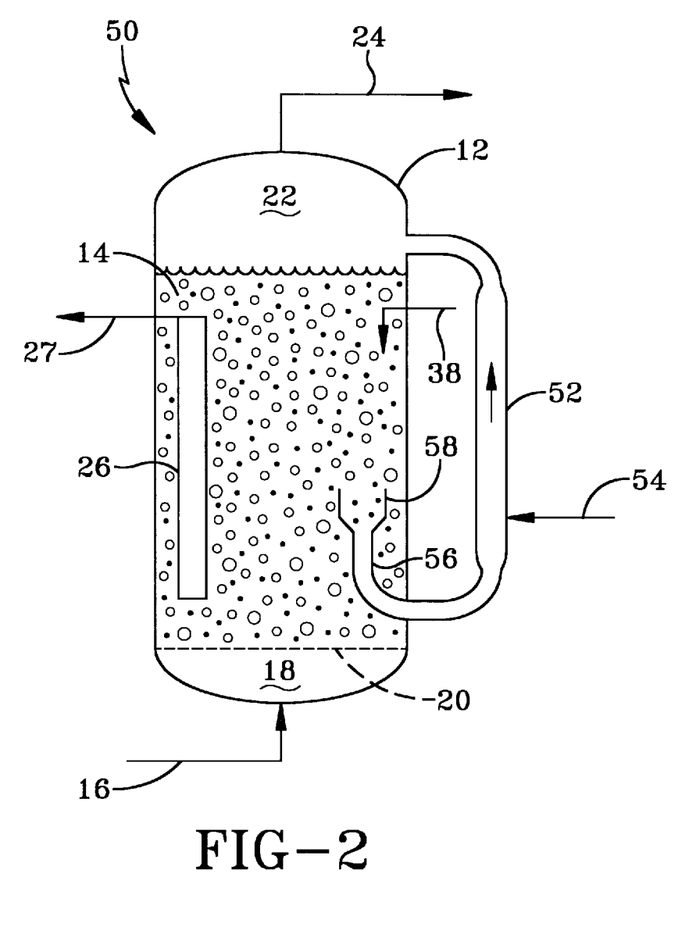
FIG. 2 is similar to FIG. 1, except that the conduit is external of the reactor.

FIG. 2 represents another embodiment of the process of the invention, in which the reaction zone for increasing the activity of fresh catalyst particles is located external of the reactor. Other than the external location of the combination activity increasing and rejuvenating lift tube reactor means, the FIGS. 1 and 2 processes are the same and the same numbers refer to the same elements. Turning to FIG. 2, slurry type hydrocarbon synthesis reactor 50 comprises a cylindrical vessel 12 having the same slurry body 14 and filter means 26 within, as in FIG. 1. However, the vertical catalyst activity increasing and rejuvenation means 52, in the form of a hollow, substantially vertically oriented fluid conduit, is located outside of the reactor, as shown. The vertical exterior portion of 52 comprises a lift tube reactor. The bottom of means 52 extends over into the reactor and up into the slurry body therein, to form a substantially vertical leg 56, having a gas bubble disengaging cup 58 at the top. The gas disengaging cup reduces the gas bubble concentration in the hydrocarbon slurry being fed from the slurry body into 52. This densifies the slurry until it contacts the hydrogen treat gas in the exterior portion of 52. The hydrogen treat gas for increasing the activity of the fresh catalyst particles and rejuvenating reversibly deactivated catalyst particles is injected up into the interior of the external vertical conduit via line 54. The interior of 52 downstream of 54 comprises the reaction zone for increasing the activity of the fresh catalyst and also for rejuvenation. The hydrogen treat gas acts as a lift gas, to ensure hydrocarbon slurry circulation up through the conduit. Thus, the interior of 52, while isolated from the slurry body in the hydrocarbon synthesis reactor, is in fluid communication with it. The lift action of the treat gas is somewhat assisted by the density-difference hydraulics created by the gas bubble removal in 58. As is the case for the process illustrated in FIG. 1, hydrocarbon slurry containing fresh catalyst particles whose activity has been increased and also rejuvenated catalyst particles, exits the top of 52 into the gas space 22 at the top of the reactor above the slurry body, to provide disengagement of the offgas in the same manner and for the same reasons given for the FIG. 1 process. While only a single combination activity increasing and rejuvenation means is shown in FIGS. 1 and 2, as a practical matter a plurality of such means will be used. As is the case for the embodiment shown FIG. 1, in the process of the FIG. 2 embodiment, one or more vertical, gas bubble disengaging downcomers of the type disclosed and claimed in U.S. Pat. No. 5,382,748 may be positioned in the slurry body in the synthesis reactor, to improve the vertical catalyst distribution. Still further, mixing means, not shown, may be present in the one or more activity increasing means or zones, to improve mixing of the hydrogen gas and slurry flowing within. However, in this and other embodiments in which the activity increasing zone is external of the synthesis reactor, in addition to the option of adding the fresh catalyst directly to the slurry body in the synthesis reactor, all or a portion of the fresh catalyst may be passed by suitable means, and typically as a slurry, directly into the one or more activity increasing tube means external of the reactor, in which it mixes with and disperses in the upflowing hydrocarbon synthesis slurry and is contacted by the hydrogen gas which increases its activity. The fresh catalyst may be passed into the external activity increasing means upstream or downstream of the hydrogen addition, or both. In this embodiment, the activity of a portion of the fresh catalyst introduced into the reactor via the external zone may not be increased, or at least not fully increased in a single pass up through the zone. The amount of time it takes for catalyst particles added to an external activity increasing zone to rise up through and out of the zone and into the slurry body of the reactor will typically be less than a minute. It takes much more time than that to introduce all the fresh catalyst into the reactor via an external activity increasing zone. Thus, even if all of the fresh catalyst is introduced into the synthesis reactor via one or more external activity increasing zones, as a practical matter and considering the time required to achieve maximum activity increase, in the context of this embodiment the slurry body is considered as containing fresh catalyst particles upon their introduction into the activity increasing zone(s). The concentration of the fresh catalyst in the slurry body continues to increase until catalyst addition ceases. At the same time, the activity of the fresh catalyst in the slurry body circulating through the means continues until the desired level of activity increase is achieved, which is typically when the overall catalytic activity reaches a maximum. In another embodiment (not shown), the lift reactor 52 may be followed by another activity increasing zone in the form of a vessel of the type shown and disclosed, for example, in U.S. Pat. No. 5,821,270 the disclosure of which is incorporated herein by reference. In such an embodiment, the activity of fresh catalyst will be increased in two, sequential external activity increasing zones.

Figure 4:
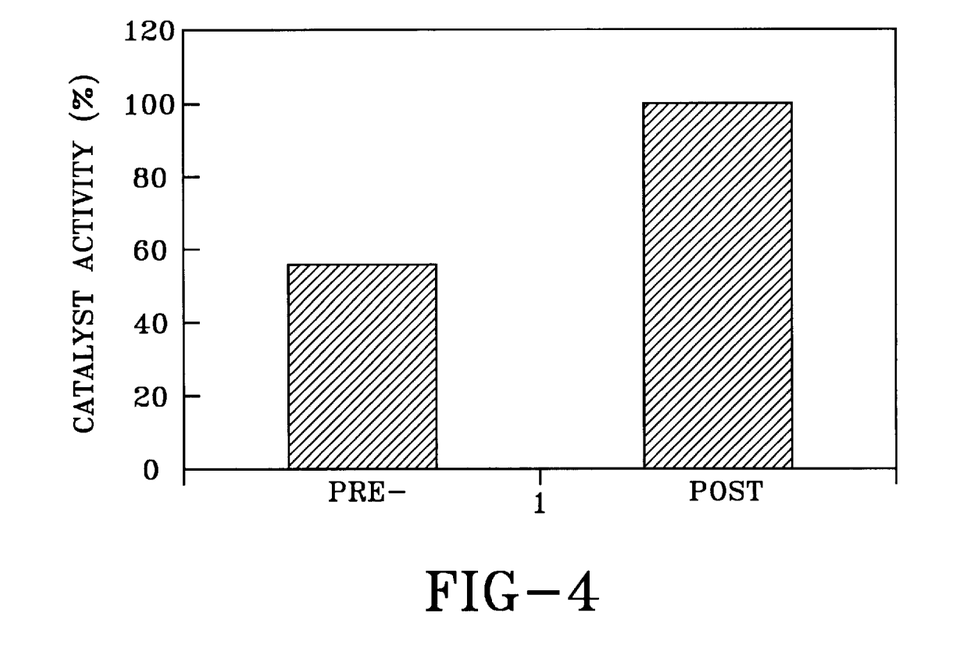
FIG. 4 graphically illustrates a prior art slurry process for increasing the activity of a fresh catalyst with the synthesis reactor off line.

It will be appreciated by those skilled in the art that means used for catalyst rejuvenation may also be used for increasing the activity of the fresh catalyst particles, with those means which include slurry gas bubble removal preferred. Additional illustrative, but non-limiting examples of such means useful in the practice of the invention are disclosed in, for example, U.S. Pat. Nos. 5,811,363; 5,811,468 and 5,958,986 the disclosures of which are incorporated herein by reference. Further and as mentioned above, if desired part or all of the hydrogen-rich offgas produced by increasing the activity of the fresh catalyst may be recovered and used as part of the treat gas after clean-up to remove contaminants. Means useful for separately recovering offgas from a lift gas reactor associated with a slurry hydrocarbon synthesis process include for example, a separate vessel downstream of the lift tube reactor which may or may not comprise a fresh catalyst activity increasing vessel, such as is disclosed, for example, in U.S. Pat. Nos. 5,958,986 and 5,821,270. Other means may comprise a shroud and offgas conduit of the type disclosed in FIG. 4 of U.S. Pat. No. 5,811,363. However, the shroud offgas overhead conduit will not pass the offgas from the catalyst activity increase reaction into the synthesis reactor offgas line, when it is desired to separately recover it. Finally, while the fresh catalyst may be introduced directly into the slurry body in the synthesis reactor in the form of solid particles, it may also be introduced as a slurry of fresh catalyst particles in a hydrocarbon liquid. However, when introduced into the synthesis reactor via one or more external activity increasing zones, the fresh catalyst particles will be dispersed in a suitable liquid, typically a hydrocarbon liquid. For a very fine particle size catalyst that may clump up and be difficult to disperse in the slurry reactor when added directly to a hydrocarbon liquid, the fresh catalyst may be slurried first in an oxygenate liquid and then in a hydrocarbon liquid as is disclosed in U.S. Pat. No. 5,977,192 the disclosure of which is incorporated herein by reference.

Hydrocarbons produced by a hydrocarbon synthesis process according to the invention are typically upgraded to more useful products, by subjecting all or a portion to fractionation and/or conversion. By conversion is meant one or more operations in which the molecular structure of at least a portion of the hydrocarbon is changed and includes both noncatalytic processing (e.g., steam cracking), and catalytic processing in which a fraction is contacted with a suitable catalyst, with or without the presence of hydrogen or other coreactants. If hydrogen is present as a reactant, such process steps are typically referred to as hydroconversion and include, for example, hydroisomerization, hydrocracking, hydrorefining and the more severe hydrorefining referred to as hydrotreating. Illustrative, but nonlimiting examples of suitable products formed by upgrading include one or more of a synthetic crude oil, liquid fuel, olefins, solvents, lubricating, industrial or medicinal oil, waxy hydrocarbons, nitrogen and oxygen containing compounds, and the like. Liquid fuel includes one or more of motor gasoline, diesel fuel, jet fuel, and kerosene, while lubricating oil includes, for example, automotive, jet, turbine and metal working oils. Industrial oil includes well drilling fluids, agricultural oils, heat transfer fluids and the like.

The invention will be further understood with reference to the examples below.

EXAMPLES

Example

In this experiment, a pilot plant hydrocarbon synthesis slurry reactor, with a production capacity in excess of one barrel per day of $C_{5+}$ hydrocarbon liquids, was used. For start-up, the reactor was loaded with a hot, Fischer-Tropsch synthesized hydrocarbon liquid free of catalyst particles. This hydrocarbon liquid was synthesized by a slurry Fischer-Tropsch process using a catalyst comprising a cobalt catalytic component and titania, under reaction conditions within the same range used in this example. It was the slurry synthesis reactor product that was liquid at the synthesis reaction conditions and had the same composition as the slurry liquid. Thus, it was synthesized from a synthesis gas comprising a 2.1:1 mole ratio of $H_2$ to CO, in the presence of a particulate Fischer-Tropsch type of hydrocarbon synthesis catalyst comprising 12 wt. % cobalt and 1 wt. % rhenium on a titania support, with an alumina-silica binder. Fresh, commercially made catalyst particles having this composition were initially activated by reduction in flowing hydrogen in a fluid bed, gassolid reactor, at temperatures up to 700° F. Following reduction, the catalyst was passivated with carbon monoxide. Then gas flow was initiated up into the reactor and the reactor heated up to about 350° F. After this, the reactor was charged with the hydrocarbon liquid referred to above, which had been heated to a temperature of about 250–300° F. Then the reactor was brought up to synthesis operating conditions, with a nominally 2.1:1 $H_2$ to CO mole ratio synthesis gas flow up into the hot hydrocarbon liquid and the passivated catalyst particles charged to the reactor, to form a three-phase hydrocarbon synthesis slurry. These conditions included a reactor outlet pressure of 275 psig., a temperature of 420° F., and a synthesis GHSV ($hr^{-1}$) of about 6600. CO conversion was maintained between 40–45%. The reactor contained a gas bubble removal, vertical catalyst rejuvenation means of the type disclosed and claimed in U.S. Pat. No. 5,817,702 immersed in the hot slurry. This was used for increasing the activity of the fresh catalyst particles during the experiment. A slurry circulating downcomer of the type disclosed in U.S. Pat. No. 5,382,748 was also immersed in the slurry liquid.

Figure 3:
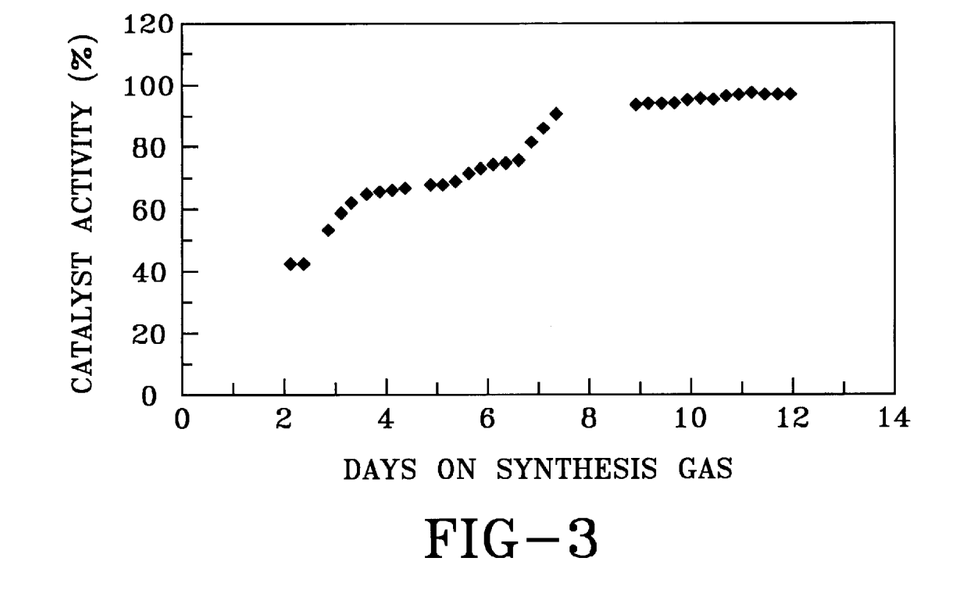
FIG. 3 is a graph of catalyst activity as a function of time employing the process of the invention.

The reactor was run at the above conditions for two days, to check the initial activity of the new catalyst. The first two points on the FIG. 3 graph represent this initial catalyst activity. The catalyst activity levels shown in FIG. 3 are all relative to the peak maximum catalyst activity level achieved by a prior art method for increasing the activity of fresh catalyst particles, similar to that disclosed in the Example in U.S. Pat. No. 5,292,705. The prior art method is given in the Comparative Example below and the results displayed in FIG. 4. After this initial activity test and before the fresh catalyst exhibited any activity loss, hydrogen flow was initiated up into the bottom of the rejuvenation tube to increase the activity of the catalyst particles in the reactor. The lifting action of the hydrogen gas in the tube caused slurry to flow down through the gas bubble removal means at the bottom and then up into, through and out the top of the lift tube, thereby creating a vertical slurry circulation through the tube and reactor. The flow rate of the hydrogen for the activity increase, up through the tube immersed in the reactive slurry, was 745 scf/hr and the slurry pumping rate was calculated to be 225 lb/hr. The gas bubble disengaging means at the bottom of the tube removed synthesis gas bubbles from the slurry liquid before it flowed up into the tube. The respective hydrogen treat rates on the catalyst and slurry in the rejuvenation tube were 5.4 scf-$H_2$Ab cat. and 2.9 scf-$H_2$/lb. During the catalyst activity increase between days 4–5 to 12 shown in FIG. 3, the slurry temperature was increased to about 435° F. at 275 psig. Unlike the method described below, in this experiment the synthesis gas flow up into the reactive slurry was maintained and the synthesis reactor was producing hydrocarbons, during the entire time that the activity of the fresh catalyst was being increased. The catalyst activity increasing hydrogen flow up into the draft tube was continued, as the reactor was synthesizing hydrocarbons, for about ten days. The reactor was run to maintain constant productivity, which means constant CO conversion per volume or weight of catalyst.

As shown by the data points in the FIG. 3 graph, the activity increasing hydrogen treatment of the invention continuously increased the catalyst activity in the reactive slurry for about eight days, after which the activity leveled out. This lined out maximum activity of the activity increased fresh catalyst achieved according to the practice of the invention, was essentially the same as the peak or maximum activity of the activity increased fresh catalyst achieved in the Comparative Example below. The initial activity prior to the activity increase was normalized to this activity increased maximum, at about 40%. This demonstrates that the fresh catalyst activity increasing hydrogen treatment of the invention resulted in more than a doubling of the initial activity of the fresh catalyst charged to the synthesis reactor. It also demonstrates that fresh catalyst particles added to a reactor equipped with catalyst activity increasing tubes or means, will have their activity increased as the synthesis reactor is operating and producing hydrocarbons from the synthesis gas feed.

Comparative Example

This experiment was conducted in the same pilot plant reactor under the same temperature and pressure and with the same catalyst composition used for the Example above. However, in this experiment, instead of using a catalyst rejuvenating tube as the means for increasing the activity of the fresh catalyst, the hydrogen for the activity increase was injected up into the slurry body in the reactor. A hydrocarbon slurry liquid produced by previous runs using the same catalyst was charged to the reactor and brought up to operating temperature. Then fresh catalyst was added to the reactor and synthesis gas flow up into the slurry of hydrocarbon liquid and fresh catalyst was initiated. After an initial run time of about eight hours to determine the initial activity of the fresh catalyst, the synthesis gas flow into the reactor was stopped, to conduct the catalyst activity increase in the absence of CO. Thus, during the activity increase, the synthesis reactor was essentially off-line, in that it was not producing hydrocarbons. The initial operating conditions included a temperature of 435° F., a pressure of 278 psig. and a GHSV of about 8400 hr$^{-1}$. After the flow of synthesis gas was stopped, hydrogen treat gas was passed up into the slurry body for one hour, to increase the activity of the fresh catalyst in the slurry. During this time, the temperature increased to 438° F., the pressure was 150 psig., the hydrogen treat rate was 24.8 scf-H$_2$/lb of catalyst and about 4 scf-H$_2$/lb slurry. Tail gas from the activity increasing reaction was recycled back and passed up through the gas distributor, in an amount adequate to maintain sufficient gas velocity up through the gas distributor or grid at the bottom of the slurry body, to prevent the catalyst particles from weeping down through the gas injection means in the distributor and to maintain catalyst particle distribution in the slurry body. After this, the synthesis gas flow was reintroduced into the slurry and the reactor brought to 395° F. at about 278 psig., a GHSV of about 8450 hr$^{-1}$ and a CO conversion of about 35–40%. The initial CO conversion achieved with the fresh catalyst, before the activity increasing treatment, was about 40% at 435° F. Thus, a nominally comparable CO conversion, at the substantially lower temperature of 395° F., was achieved by the activity increased catalyst. The difference in hydrocarbon synthesis catalyst activity, before and after this prior art fresh catalyst activity increasing treatment, is shown in the FIG. 4 graph, in which the activities are normalized to the maximum enhanced or increased catalyst activity being defined as 100%.

It is understood that various other embodiments and modifications in the practice of the invention will be apparent to, and can be readily made by, those skilled in the art without departing from the scope and spirit of the invention described above. Accordingly, it is not intended that the scope of the claims appended hereto be limited to the exact description set forth above, but rather that the claims be construed as encompassing all of the features of patentable novelty which reside in the present invention, including all the features and embodiments which would be treated as equivalents thereof by those skilled in the art to which the invention pertains.

What is claimed is:

1. A process for increasing the activity of a fresh, supported cobalt hydrocarbon synthesis catalyst in a hydrocarbon synthesis slurry comprises (i) contacting said slurry with a hydrogen treat gas in one or more catalyst activity increasing zones, to increase the activity of said fresh catalyst, and (ii) passing said slurry containing said activity increased catalyst into a slurry body in a hydrocarbon synthesis reactor while said reactor is producing hydrocarbons from synthesis gas, and wherein said slurry body comprises a hydrocarbon synthesis slurry comprising hydrocarbon synthesis catalyst particles and bubbles of synthesis gas in a hydrocarbon slurry liquid.

2. A process according to claim 1 wherein said one or more activity increasing zones are at least partially immersed in said slurry body in said reactor, are exterior of said reactor or both.

3. A process according to claim 2 wherein at least a portion of said gas bubbles are removed from said hydrocarbon synthesis slurry before it is passed into said one or more activity increasing zones.

4. A process according to claim 3 wherein said hydrocarbon synthesis slurry containing said fresh catalyst during said contacting comprises slurry obtained from said slurry body.

5. A process according to claim 4 wherein said hydrocarbons produced from said synthesis gas comprises hydrocarbons that are liquid at the synthesis reaction conditions and which comprise said slurry body slurry liquid.

6. A process according to claim 5 wherein said hydrocarbon synthesis slurry contains reversibly deactivated catalyst particles which are at least partially rejuvenated in said activity increasing zone.

7. A process according to claim 6 wherein at least a portion of said slurry body slurry liquid is withdrawn from said reactor and is sent to one or more upgrading operations comprising at least one of (i) fractionation and (ii) a conversion operation in which the molecular structure of at least a portion of the hydrocarbon molecules is changed.

8. A process according to claim 7 wherein said activity increasing zone comprises a lift gas reaction zone comprising the interior of a substantially vertically oriented, elongated hollow fluid conduit open at the top and bottom for said slurry and treat gas to flow through.

9. A process according to claim 8 wherein said hydrogen treat gas acts as a lift gas in said one or more zones, to produce slurry circulation from said slurry body into said zone and back into said body, wherein said treat gas contains less than 10% CO, wherein the mole ratio of said hydrogen to CO in said gas is greater than 3:1, and wherein said catalyst comprises a catalytic cobalt component.

10. A slurry hydrocarbon synthesis process comprises:
  (a) passing a synthesis gas comprising a mixture of H$_2$ and CO up into a slurry body comprising a hydrocarbon synthesis slurry, in a hydrocarbon synthesis reactor, wherein said slurry comprises a particulate Fischer-Tropsch catalyst and bubbles of the synthesis gas dispersed in a hydrocarbon liquid, at reaction conditions effective for said H$_2$ and CO in said synthesis gas to react and form hydrocarbons, at least a portion of which are liquid at the reaction conditions and which comprise the slurry hydrocarbon liquid;
  (b) adding fresh, supported cobalt catalyst particles to said hydrocarbon synthesis slurry, and
  (c) passing a hydrogen treat gas and said hydrocarbon synthesis slurry containing said fresh catalyst particles through one or more activity increasing zones, in which the hydrogen in said treat gas contacts said fresh catalyst particles in said slurry, which increases the activity of at least a portion of them, wherein said slurry containing said activity increased catalyst exits said one or more zones and is passed into said slurry body in said reactor, and wherein said activity increasing occurs while said synthesis reactor is producing hydrocarbons from said synthesis gas.

11. A process according to claim 10 wherein said one or more activity increasing zones are at least partially immersed in said slurry body in said reactor, are exterior of said reactor or both.

12. A process according to claim 11 wherein at least a portion of said gas bubbles are removed from said slurry before it is passed or circulated into said one or more zones.

13. A process according to claim 12 wherein said fresh catalyst particles are added to said slurry body or to said slurry passing through said one or more activity increasing zones.

14. A process according to claim 13 wherein said slurry body contains partially and reversibly deactivated catalyst particles, which are at least partially rejuvenated in said activity increasing zone during said activity increase.

15. A process according to claim 14 wherein a portion of said synthesized hydrocarbon liquid is continuously or intermittently withdrawn from said reactor and is sent to one or more upgrading operations comprising at least one of (i)

fractionation and (ii) a conversion operation in which the molecular structure of at least a portion of the hydrocarbon molecules is changed.

16. A process according to claim 15 wherein said circulation and contacting with said hydrogen in said one or more zones continues for a time sufficient to increase the activity of said fresh catalyst particles added to said reactor, as evidenced by a peak in catalytic activity.

17. A process according to claim 15 wherein said activity increasing zone comprises a lift tube reaction zone and wherein said hydrogen treat gas acts as a lift gas in said zone to provide slurry circulation from said slurry body into said zone and back into said slurry body.

18. A process according to claim 17 wherein said zone comprises the interior of a substantially vertically oriented, elongated hollow fluid conduit open at the top and bottom for slurry to flow through.

19. A process according to claim 18 wherein said treat gas contains less than 10% CO and wherein the mole ratio of said hydrogen to CO in said gas is greater than 3:1.

* * * * *